United States Patent [19]

Nagasaki et al.

[11] Patent Number: 5,056,503
[45] Date of Patent: Oct. 15, 1991

[54] ENDOSCOPE WITH HIGH FREQUENCY ACCESSORY AND REDUCED VIDEO INTERFERENCE

[75] Inventors: Tatsuo Nagasaki, Musashino; Hiroyoshi Fujimori, Hachioji, both of Japan

[73] Assignee: Olympus Optical Co., Ltd., Tokyo, Japan

[21] Appl. No.: 658,419

[22] Filed: Feb. 28, 1991

Related U.S. Application Data

[63] Continuation of Ser. No. 494,834, Mar. 16, 1990, abandoned, which is a continuation of Ser. No. 161,276, Feb. 22, 1988, abandoned, which is a continuation of Ser. No. 915,876, Oct. 8, 1986, abandoned, which is a continuation of Ser. No. 657,274, Oct. 3, 1984, abandoned.

[30] Foreign Application Priority Data

Oct. 3, 1983 [JP] Japan ................................ 58-184684

[51] Int. Cl.$^5$ ...................... A61B 17/32; A61B 1/06
[52] U.S. Cl. ............................................ 128/6; 128/4; 606/42; 606/46
[58] Field of Search ........................................ 128/4–6; 606/34, 41, 42, 45, 46

[56] References Cited

U.S. PATENT DOCUMENTS

| | | | |
|---|---|---|---|
| 4,054,797 | 10/1977 | Milton et al. | 250/370 G |
| 4,074,306 | 2/1978 | Kakinuma et al. | 128/6 |
| 4,115,692 | 9/1978 | Balcerak et al. | 250/370 G |
| 4,176,275 | 11/1979 | Korn et al. | 251/370 G |
| 4,253,447 | 3/1981 | Moore et al. | 128/6 |
| 4,327,738 | 5/1982 | Green et al. | 128/6 |
| 4,331,873 | 5/1982 | Miller et al. | 250/370 G |
| 4,423,325 | 12/1983 | Foss | 250/370 G |
| 4,473,841 | 9/1984 | Murakoshi et al. | 128/6 |
| 4,480,636 | 11/1984 | Karaki et al. | 128/6 |
| 4,487,489 | 12/1984 | Takamatsu | 128/6 |
| 4,509,508 | 4/1985 | Tsukaya | 128/6 |
| 4,517,976 | 5/1985 | Murakoshi et al. | 128/4 |
| 4,519,391 | 5/1985 | Murakoshi | 128/4 |
| 4,532,918 | 8/1985 | Wheeler | 128/6 |
| 4,561,429 | 11/1985 | Sato et al. | 128/6 |
| 4,588,927 | 5/1986 | Kanno et al. | 128/6 |
| 4,590,924 | 5/1986 | Tanikawa et al. | 128/6 |
| 4,615,330 | 10/1986 | Nagasaki et al. | 128/4 |
| 4,646,724 | 3/1987 | Sato et al. | 128/6 |
| 4,653,478 | 3/1987 | Nagasaki et al. | 128/6 |

FOREIGN PATENT DOCUMENTS

56235 7/1982 European Pat. Off. ....... 128/303.15

OTHER PUBLICATIONS

"Electronics Engineers' Handbook", Third Edition, Donald G. Fink and Donald Christiansen, Editors, McGraw-Hill Book Company (1989).
"ITV Camera", Kotaro Wakui, Japan Broadcasting Publishing Associated Press (1973).
"Color Video Camera", Masa Kazu Hara, Japan Broadcasting Publishing Associated Press (1986).

*Primary Examiner*—David Shay
*Attorney, Agent, or Firm*—Armstrong, Nikaido, Marmelstein, Kubovcik & Murray

[57] ABSTRACT

An endoscope incorporating a solid state image pickup element for picking-up optical images of an object under observation, and an accessory means having a high frequency oscillator, is able to perform imaging and an accessory function without mutual interference due to high frequency noise from the accessory means oscillator affecting the imaging signals. The output of high frequency oscillation in the accessory means is inhibited during a signal reading period of the image pickup element by a control pulse sychronized with the application of clock signals to the image pickup element.

8 Claims, 3 Drawing Sheets

FIG.1
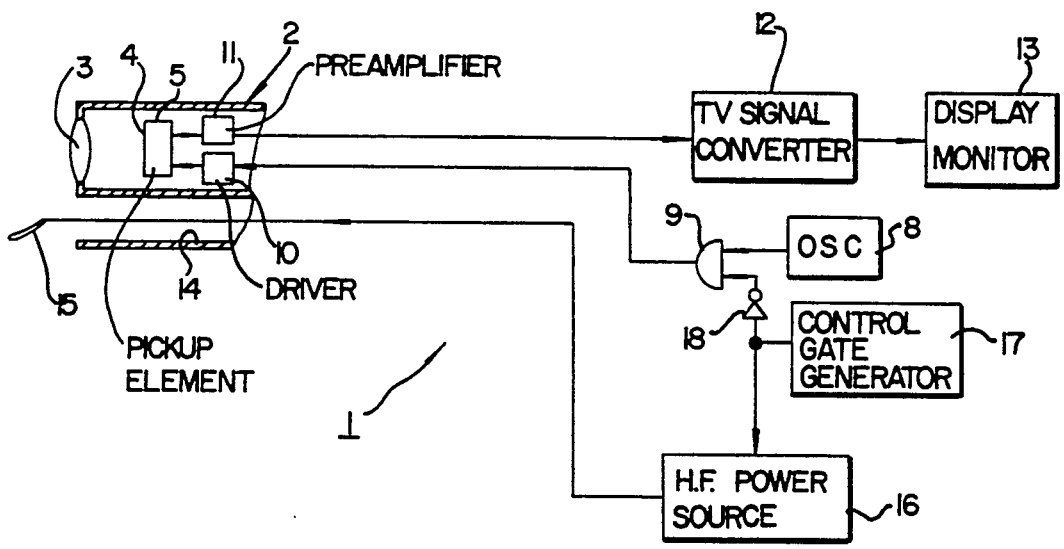
FIG.2
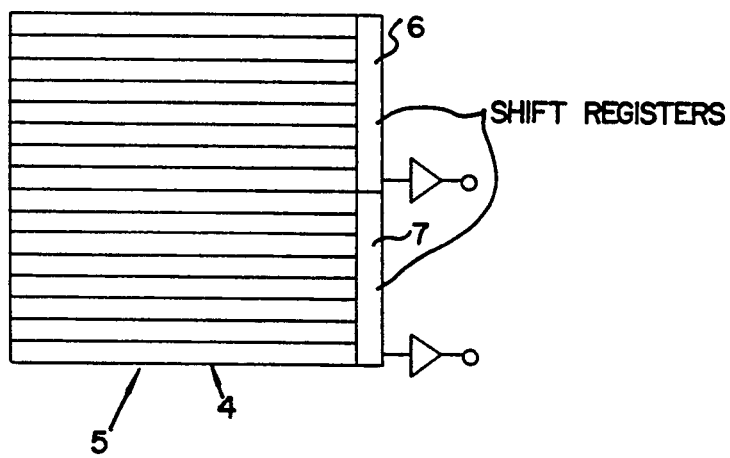
FIG. 3(a)   CONTROL GATE SIGNAL
FIG. 3(b)   OSC OUT
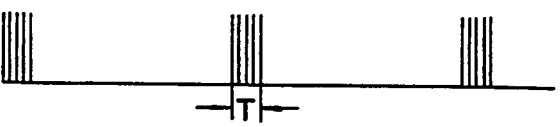
FIG. 3(c)   CLOCK

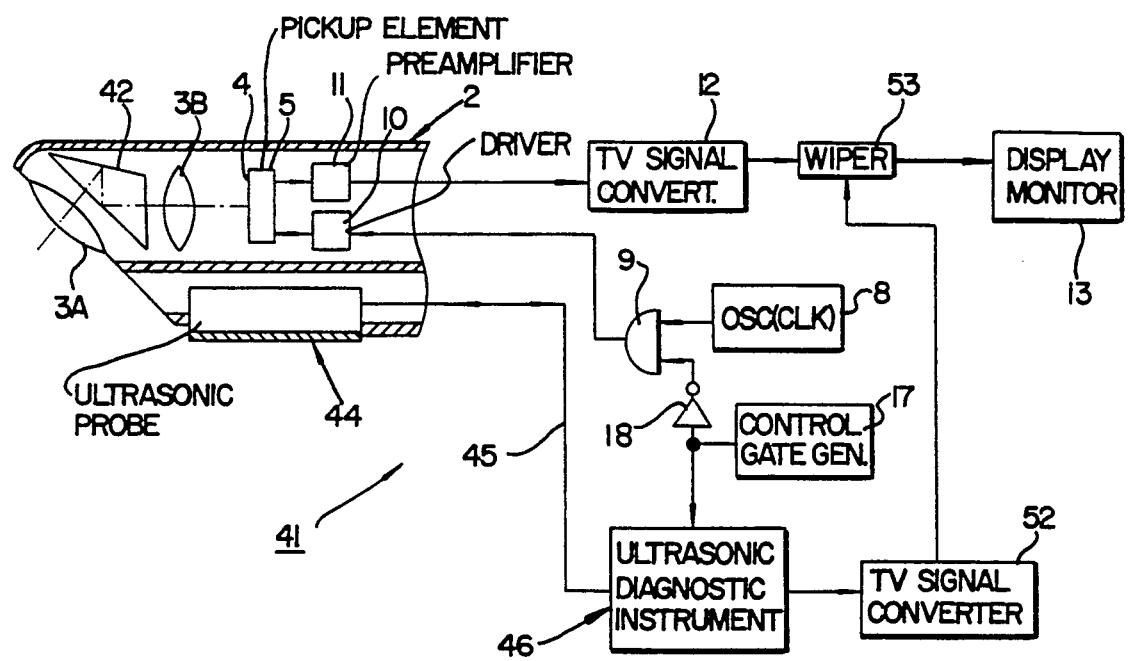
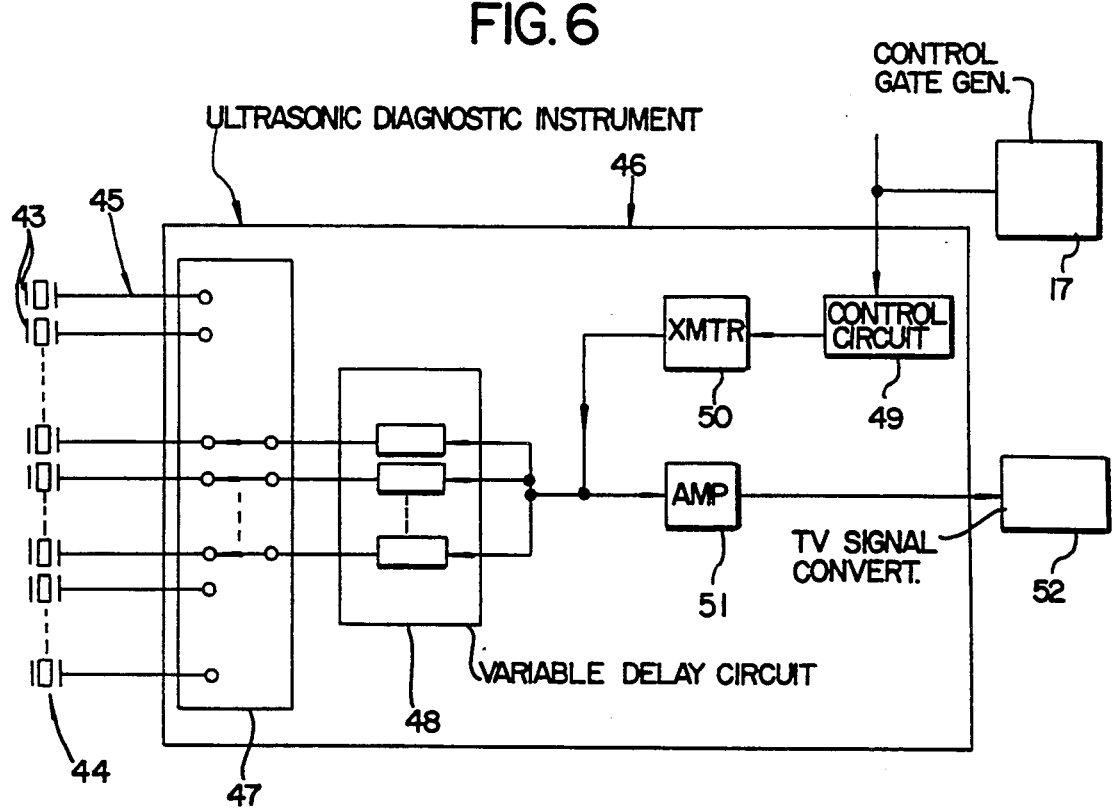

ENDOSCOPE WITH HIGH FREQUENCY ACCESSORY AND REDUCED VIDEO INTERFERENCE

This application is a continuation of application Ser. No. 494,834 filed Mar. 16, 1990 now abandoned, which is continuation of Ser. No. 161,276 filed Feb. 22, 1988 now abandoned, which is continuation of Ser. No. 915,876 filed Oct. 8, 1986 now abandoned, which is a continuation of Ser. No. 657,274 filed Oct. 3, 1984 now abandoned.

BACKGROUND OF THE INVENTION

The present invention relates to endoscope incorporating a solid state image pickup element for picking up images and functioning without mutual interference with other functioning attached to the endoscope means such as a high frequency surgical knife or the like.

There have been proposed various endoscope means incorporating a solid state image pickup means such as charge-coupled devices (CCD) as image pickup means.

When a diseased portion is surgically treated, by a surgical knife coupled with the CCD as an image pickup means, the high frequency electromagnetic waves, of the surgical knife used for cutting the diseased portion, leak to the output signal of each of the receiver elements of the CCD to cause the leaked signal to be recorded and to produce noise in the image display so as to make the image obscure, thereby disadvantageously making observation and optimum surgical treatment difficult.

In addition, when a DC-DC converter having a high conversion efficiency is used for completely insulating the portion of the endoscope means inserted into the body cavity from the power source for safe operation, the image may be distorted by the contamination of output signals from the receiver elements with high frequency electromagnetic waves output by the DC-DC converter.

Furthermore, when the endoscope means is equipped with an ultrasonic vibrator as an ultrasonic endoscope means for enabling ultrasonic diagnosis, the output signals from the ultrasonic vibrator may be mixed disadvantageously into the output signals from the optical image pickup receiver elements.

BRIEF SUMMARY OF THE INVENTION

It is a primary object of the present invention to provide endoscope means incorporating a solid state image pickup means capable of use for another function such as a high frequency surgical knife or the like substantially without any trouble, and to inhibit the contamination of picked-up image signals by noise produced from said other function.

It is another object of the present invention to provide an endoscope means incorporating a solid state image pickup means and which is compatible with an electrical instrument producing noise which effects the pick-up means.

Other features and advantages of the present invention will be elucidated clearly from the following description.

BRIEF DESCRIPTION OF THE DRAWINGS

FIGS. 1 to 3 relate to a first embodiment of the present invention wherein FIG. 1 is a block diagram showing the outlined structure of endoscope means according to the first embodiment; FIG. 2 is a schematic view showing the structure of solid state pickup means of the line transmitting type employed in the first embodiment; and FIG. 3 is a timing chart for illustrating the operation of the first embodiment.

FIGS. 5 and 6 relate to a third embodiment of the present invention wherein FIG. 5 is a block diagram showing the outlined structure of the third embodiment, and FIG. 6 is a block diagram showing the ultrasonic diagnostic means of the third embodiment.

DETAILED DESCRIPTION OF THE EMBODIMENTS

Figure 4:
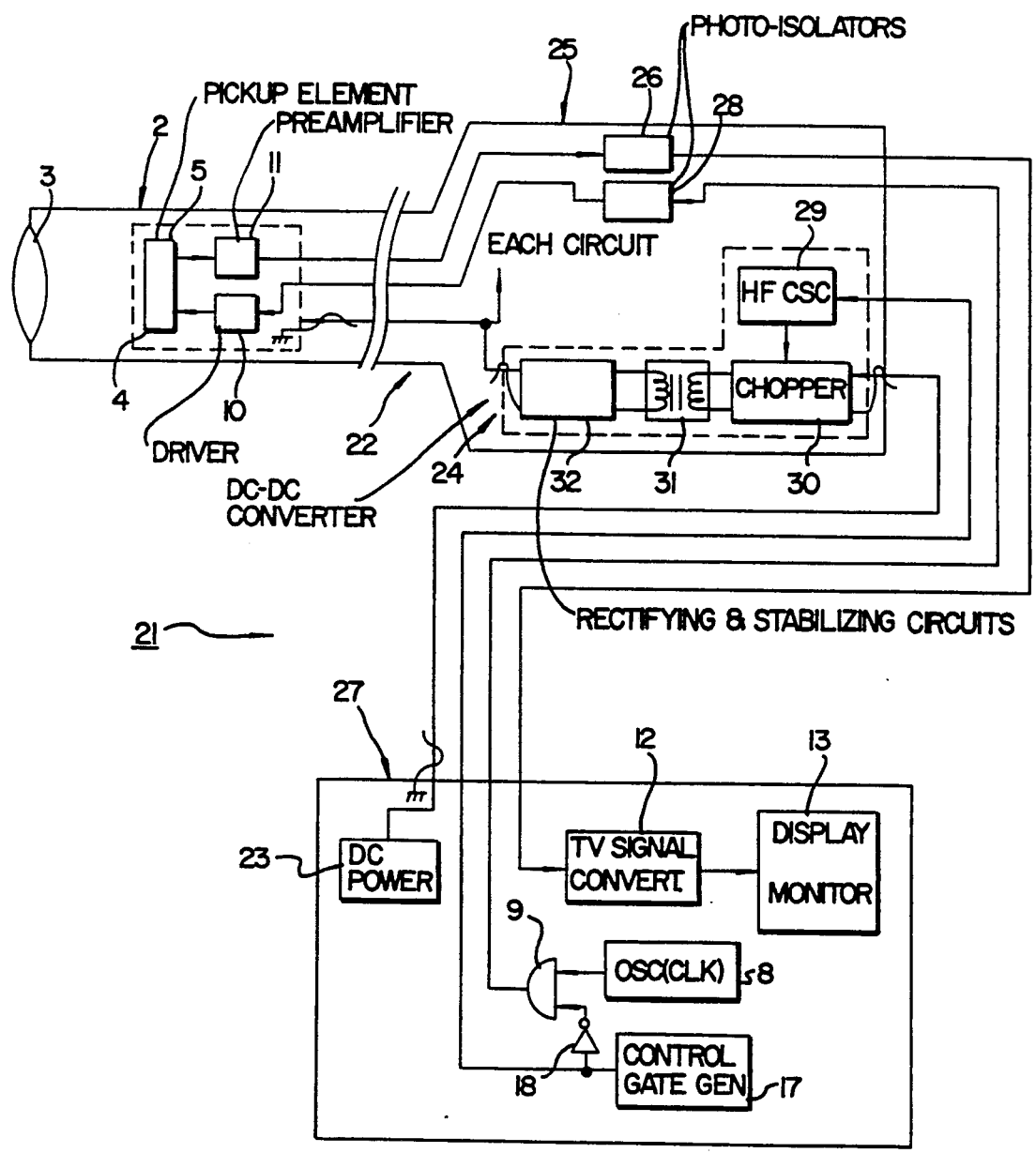
FIG. 4 is a block diagram showing the outlined structure of a second embodiment.

As shown in FIG. 1, endoscope means 1 of the first embodiment are provided with image pickup means at a rigid tip connected to the end of an elongated and flexible insertion member 2 for insertion into a body cavity or the like.

An objective lens 3 for forming images, is attached at the opening defined at the tip of insertion member 2 and a solid state image pickup element 5 of the line transmitting type is mounted so that the focal plane (receiver plane) 4 thereof coincides with the focal plane of the objective lens 3.

The focal plane 4 of the solid state image pickup element 5 of the line transmitting type is formed by arranging a great number of receiver elements (photosensitive elements), having photoelectrical conversion capability in regular rows as shown in FIG. 2. Charge signals, received by each of the receiver elements prior to the application of clock signals thereto and stored as electrical charges, are successively transmitted one after another so as to shift the stored charges horizontally under application of the clock signals. The signals are read out through output shift registers 6, 7. In short, the solid state image pickup element 5 of the line transmitting type is able to be miniaturized due to its capability of combined action as receiver and transmitter as compared with elements of other types.

Still further, in this embodiment, the reading out period is shortened by dividing the output into the dual channels employing output shift registers 6, 7.

The clock signals for reading out the outputs are generated from an oscillator 8 and supplied through a control-gate by an AND circuit 9 to a driver 10 wherein the signal is applied to solid state image pickup element 5 as the clock signal during a predetermined transmitting phase.

There is attached, for example, a mosaic tri-color filter at the front of the pickup plane of the solid state image pickup element 5 and the output signals from each of the receiver elements are thereby converted to colored picture image signals. The read-out picture signals are amplified through a preamplifier 11 with low noise characteristics, and applied to a television (TV) signal converter means 12 at the trailing end of the insertion member, and stored in a frame memory formed, for example, with two memory capacities each for ½ of a picture frame, in TV signal converter means 12. The signals stored in each frame memory are passed through matrix circuits and mixing circuits for each frame. The signals are overlapped with the horizontal and vertical sync signals in order to be converted into television signals, for example, for a predetermined NTSC system. The signals are then displayed on the cathode ray tube of a monitoring color television picture tube 13.

There is a channel 14 formed for inserting a surgical instrument in the insertion member 2 so that surgical operations such as cutting can be performed by a high frequency surgical knife 15 used as an instrument employed in combination with the endoscope means and inserted through the channel 14.

The high frequency surgical knife 15 is supplied with high frequency waves of, for example, several hundred KHz, from a power source 16 for the high frequency surgical knife. The control terminal of power source 16 for the high frequency surgical knife is supplied with control-gate signals as shown in FIG. 3(a) from a control-gate generator means 17 and when the control-gate signals are at a high level, power source 16 supplies power for the high frequency surgical knife cutting output (c.f. FIG. 3(b)) and when the control-gate signals are low level, the supplying of cutting output power is stopped. The high and low levels of the control-gate signals are repeated in sychronization with the pickup function of solid state image pickup element 5.

In other words, high frequency output inhibitor means are structured so that the control-gate signals are applied through an inverter 18 to another input terminal of the AND circuit 9, and a short clock time T for reading the picture signals from each receiver element of the solid state image pickup element 5 (c.f. FIG. 3(c)) is set to be within the low level control-gate signal period duration when no high frequency output is supplied for the surgical operation, by means of the oscillator 8. Accordingly, during the reading of picture element signals, particularly within the bandwidth, the picture element signals include only their frequency components and no high frequency causing noise is output, thereby preventing the degradation of picture quality. (In addition, since the reading is carried out within short clock time T, the bandwidth is extended to the high frequency side as compared with the bandwidth to be actually displayed. Moreover, the clock time T for stopping the high frequency output is, for example, as short as 4 m sec. in a cycle of 33 m sec. and the high frequency output is supplied for a residual 29 m sec. so that the cutting function by means of the high frequency surgical knife 15 can be achieved smoothly.

Within the insertion member 2, a light guide formed by a flexible optical fibre bundle (not shown) is inserted therethrough in contact with objective lens 3 and the trailing end of the light guide is detachably connected with a light source means (not shown) so that the trailing end of the light guide is irradiated by the illuminating light from the light source's incandescent lamp. The irradiated light illuminates the area of an object to be picked up and focused on the focal plane by means of the objective lens 3 through the leading end of the light guide.

Still further, the illuminating lamp is designed so as to be energized only during the period when the control-gate signals are at a high level. In addition, the application of control-gate signals to the control terminal of the power source means 16 for the high frequency surgical knife can be ON-OFF controlled by a switch (not shown).

According to the first embodiment of the present invention structured as mentioned hereinabove, when a high frequency surgical knife 15 is to be operated, the switch is turned to ON to set the condition enabling the application of the control-gate signals to the control terminal of power source means 16 for the high frequency surgical knife, thereby irradiating the illuminating light on to the object, such as a diseased portion, to be imaged, and storing an image of the object focused on the focal plane 4 and received as incident light by means of each receiver element to form electrical charges during the high level of the control-gate signals, while surgically treating the diseased portion to be cut by means of the high frequency surgical knife 15 supplied with high frequency output. During the clock time T for reading the received and stored charges, the control-gate signals are turned to the low level, the clock signals are applied from oscillator 8 through AND circuit 9 to driver 10 and the output signals from each receiver element are picked up through two shift registers 6, 7 successively within a short period, amplified through preamplifier 11 and stored in the frame memories in TV signal converter means 12. During the clock time T, the high frequency output is stopped so that there is no possibility of contamination of the high frequency output into the stored picture elements and the image signals of the picture elements are stored under the condition of a higher signal-t noise ratio. In addition, the illuminating light is de-energized during the time T so that no smear occurs during the reading of picture elements. After the termination of storage of the picture element signals for one image frame, the control-gate signal is turned to the high level, the above-mentioned illumination is restarted and the high frequency output is applied to high frequency surgical knife 15 to permit the surgical operation.

During this period, the picture elements stored in the frame memories within TV signal converter means 12 for the one image frame are converted into television signals for a monitoring color television of the NTSC type, to be displayed on monitoring color TV picture tube 13.

According to the first embodiment functioning as disclosed hereinbefore, during the high level period of the control-gate signals, each receiver element of solid state image pickup element 5 receives incident light on each imaging element and accumulates a charge signal for forming an image, and the high frequency output is applied to high frequency surgical knife 15; and during short clock time T during the low level period of the control-gate signal, the stored signals in each receiver element are read through the two output channels and the high frequency oscillator for the surgical operation is stopped so that the imaging operation can be performed without the imaging signal being contaminating by noise.

In addition, the TV signals output after the conversion through TV signal converter means 12 are sufficiently amplified during writing into the frame memories, so that they are not substantially effected by the high frequency waves, so as to provide a distinct image. When the R, G, B signals are applied directly to the input terminals of R, G, B inputs in such a case, an image of higher quality can be provided than when the signals are modified by means of carrier wave modulation techniques.

In the endoscope means 21 in the second embodiment as shown in FIG. 4, since a DC power source means 23 for rectifying and stabilizing a commercial power source is used as a power source for the image pickup and the like, no sufficient isolation from the commercial power source is provided, so that a DC-DC converter 24 is interposed for achieving complete isolation.

The second embodiment is being illustrated by attaching the same reference numerals to the same elements corresponding to the first embodiment.

The output signals are amplified through preamplifier 11 and applied through a photoisolator 26 such as a photocoupler or the like in an operator means 25 to the input terminal of TV signal converter means 12 in a displaying means 27 provided externally of the operator means 25. The clock signals issued from AND circuit 9 of oscillator 8 are passed through a photoisolator 28 in operator means 25 to driver 10.

Moreover, each input terminal of solid state image pickup element 5, preamplifier 11, driver 10, etc. is connected to the output terminal of DC-DC converter 24 installed in operator means 25.

The DC-DC converter 24 receives the DC power output from a DC power source means 23 in displaying means 27 and the high frequency output from an oscillator 29 is fed to a chopper 30 to control the wave form to be applied to the primary side of an isolation transformer 31 having high insulation resistance. The AC current induced at the secondary side is rectified through rectifying and stabilizing circuits 32 to produce stabilized output.

Further, oscillator 29 in said DC-DC converter 24 is supplied at a control terminal thereof with the control-gate signal and high frequency output inhibitor means are provided so that the oscillator is actuated during the high period of the control-gate signals and ceases its oscillation during the low level period of the signals.

According to the second embodiment structured as disclosed hereinabove, when the control-gate signals are at the high level, the image of an illuminated object is focused on the focal plane 4 and each receiver element receives one picture element and stores the electrical charge corresponding to the received light intensity. During this period, oscillator 29 in the DC-DC converter 24 is actuated to supply the power to rectifying and stabilizing circuits 32 and a portion of the power is stored in a capacitor (not shown).

When the control-gate signals are turned to the low level, the electrical charge stored in each receiver element is read through photoisolator 28 within short clock time T and the read signals are applied through photoisolator 26 to TV signal converter means 12.

Since the oscillator 29 in DC-DC converter 24 is deactivated during this period, the components within the band of read signals are protected from contamination by noise. Moreover, since the time is short similarly to the first embodiment, the required power can be assured by the power stored before this period, even if no power is supplied to the rectifying and stabilizing circuits 32.

Accordingly, the image pickup means and DC-DC converter 24 can be operated without unfavorable mutual interference and without any trouble.

Because of the isolation of DC-DC converter 24 from the power source means, and of endoscope means 22 from displaying means 27 whereby signal transmission is carried out by means of photoisolators 26, 28 in the second embodiment, endoscope means 22 are isolated completely from the power source line of displaying means 27 to make the means safe. In addition, DC-DC converter 24 and photoisolators 26, 28 can be miniaturized sufficiently, so that they can be received in operator means 25.

FIG. 5 illustrates an ultrasonic endoscope means 41 (ultrasonic diagnostic instrument) as an endoscope means according to the third embodiment of the present invention.

The ultrasonic endoscope means are composed of an optical pickup system of the perspective type wherein the tip of the insertion member is opened obliquely to the forward direction and an image of an object positioned obliquely forwards or at the vicinity thereof can be focused through a prism 42 and an objective lens system 3A, 3B onto focal plane 4 of solid state image pickup element 5.

As shown in FIG. 6, there is an ultrasonic probe 44 formed by arranging a great number of ultrasonic vibrators 43, . . . , 43 attached at the side of the tip for linearly electronically scanning. Each electrode of said ultrasonic vibrators, 43, . . . , 43 is connected successively to form a set comprising a plurality of the vibrators, say, 8 vibrators, by means of an electronic switch 47 in an ultrasonic diagnostic instrument 46 provided inside or outside of the operator means through a lead wire bundle 45 and the actuated vibrators 43 are supplied with high frequency pulses output from a transmitter means 50, the transmitting period of which is controlled by means of a control circuit 49 through a variable delay circuit 48 so as to emit a high frequency pulse output, and the vibrators receive the reflective ultrasonic waves during a receiving period when the transmission of high frequency pulses has been stopped and feed the reflection signals to an amplifier means 51. (Another electrode of each vibrator 43 is grounded.)

The signals amplfied through the amplifier 51 are passed through a TV signal converter means 52 and a wiper 53 also connected to TV signal converter 12, so as to display the output signals from TV signal converter means 12 of the optical image pickup means and the ultrasonic image in two split zones such as right or left zones of the image on the same screen on monitor color TV picture tube 13.

The variable delay circuit 48 is set so that the delay time for each of the plurality of activated vibrators 43, . . . , 43 differs slightly from one to another for focusing electronically by arranging the transferred wave fronts in a concave plane with respect to a predetermined direction during the sector scanning or the like to provide an ultrasonic diagnostic image having high resolving power.

The control terminal of said control circuit 49 is supplied with the control-gate signal from the control-gate means 17 and during the high level period of the control-gate signals, control circuit 49 controls transmitter 50 and amplifier means 51 under normal conditions to transmit the ultrasonic waves and to receive the reflected ultrasonic rays; and during the low level period of said signals, ultrasonic output inhibitor means are formed so that the control circuit does not output control signals from control circuit 49 for permitting transmission of the ultrasonic waves.

According to the third embodiment structured as disclosed hereinabove, during the picking-up period of the optical image pickup means, the high frequency pulses for transmitting the ultrasonic waves are not output from transmitter means 50 so that the read signals can be protected from the contamination of high frequency pulses from transmitter means 50 as noise. Moreover, during the receiving period of the reflected ultrasonic waves, solid state image pickup element 5 is not supplied with the reading clock output to prevent the contamination of the clock signals into the weak signals received on the solid state image pickup element, and to eliminate the unfavorable mutual interference.

Moreover, although said third embodiment has been disclosed hereinabove for the electronic sector scanning, it can be accommodated to any scanning type such as linearly translated scanning, arc scanning or the like and not only to the axial arrangement but also to the peripheral arrangement of ultrasonic vibrators, 43 . . . , 43 with respect to the tip of insertion member 2. It is also accommodated not only to the electronic scanning type but also to the mechanical scanning wherein the ultrasonic vibrators or an ultrasonic mirror are rotated or pivoted by means of a motor or other rotating or pivoting means.

Still further, the optical pickup system is not limited to the perspective type but can be accommodated to the side-vision or direct vision type.

Still further, though the color image picking-up is performed by employing a three-colored mosiac filter attached at the front of focal plane 4 of solid state image pickup element 5 in each of said embodiments, the present invention is not limited to the employment of a three-colored mosaic or stripe filter but is compatible with the case wherein the object is illuminated successively by light having colors having three wave lengths and output from the illuminating means and wherein the image pickup receives the light using a monochroic solid state pickup element under the illumination of each colored light, stores the signals in each colored frame memory and displays the monochroic signals successively with each colored image or displays concurrently signals stored in each colored frame memory, or the like.

Still further, in each of said embodiments, solid state image pickup element 5 incorporates two output shift registers 6, 7 as shown in FIG. 2 to read the output signals concurrently from the two output terminals so as to reduce the signal reading period as compared with a case wherein a single output terminal is employed. In order to reduce the period further, the number of output shift registers and output terminals may be increased to increase the number of channels and the present invention includes embodiments wherein solid state image pickup elements having more than three channels are employed. In addition, there are cases wherein a single output terminal may achieve the requirements and the present invention can be accommodated to solid state image pickup elements having structures for reading the signals from a single output terminal. Still further, the above mentioned embodiments employ the solid state image pickup element 5 of the line-transferring type but the present invention may employ a solid state image pickup element of the frame transferring type or the vertical interline type and other solid state image pickup elements other than a CCD type.

It is obvious that the present invention includes combinations of said embodiments.

Still further, oscillators 8 output high frequency waves only during the clock period T and are not actuated during the periods when accessory means of the endoscope means (other than the pickup means) are outputting high frequency waves. The present invention includes such an embodiment. The present invention includes also such embodiments wherein the oscillation which may form noise is stopped or not transmitted to the load side during the clock period T for an accessory function other than the picking-up of an image.

As set forth hereinbefore, in the endoscope means employing a solid state pickup element according to the present invention, the signal reading period from each receiver element is shortened and during this short period no oscillating wave is applied from accessory means, such as a high frequency surgical knife, DC-DC converter, ultrasonic diagnostic instrument, etc., using an output from an oscillator containing frequency components within the pickup element's signal bandwith and attached to the endoscope means, so that the read signals are free from noise and are distinct. In addition, as said signal reading period or period of inhibited output of oscillating waves is designed to be sufficiently short, each functioning means can be operated sufficiently without any trouble.

Furthermore, oscillating output inhibitor means can be formed by a simple structure using the control-gate pulse in synchronization with said signal reading period. In addition, oscillating output inhibitor means can be provided by a substantially equal mechanism for accessory means having a different mechanism for the endoscope means.

It is obvious to invent various embodiments within a wide range on the basis of the present invention without departing from the spirit and scope of the present invention.

Accordingly, the present invention should not be limited to any embodiments except the ranges as specified by the attached claims.

We claim:
1. An endoscope comprising:
   an elongate insertion member insertable within a body cavity;
   an image-forming optical system disposed at a tip of said insertion member, said image-forming optical system for forming an image of an object under observation on a focal plane thereof;
   illuminating means for illuminating an object to be imaged within an image-forming range of said image-forming optical system;
   a solid state optical image pickup having a plurality of photo-electrically converting receiver elements each arranged on a pickup plane coinciding with said focal plane of said image forming optical system, said solid state optical image pickup producing picture element signals corresponding to an image formed thereon;
   driving circuit means connected with said solid state optical image pickup, said driving circuit means for applying clock signals to said solid state optical image pickup in order to read out said picture element signals during a reading period;
   frame memory means connected with said solid state optical image pickup, said frame memory means for storing read out picture element signals;
   television signal converter means connected with said frame memory means for reading out said picture element signals written in said frame memory means and for converting said read out picture element signals into video signals of a predetermined television signal format;
   display means connected with said television signal converter means, said display means for displaying said video signals as a television picture on a display monitor;
   accessory means for being locatable through said insertion member;

high frequency oscillation means for driving said accessory means, said high frequency oscillation means for producing high frequency components within a band when said pickup element signals are read out of said solid state optical image pickup;

gate means connected to said driving circuit means, said gate means for gating clock signals of said driving circuit means during a read out period of said solid state optical image pickup; and control gate generator means for supplying high and low levels of control gate signals in repeated synchronization with a pickup function of said solid state optical image pickup, said control gate generator means being connected to said gate means and said high frequency oscillation means in order to inhibit an operation of said accessory means only during said reading period;

wherein said reading period is of shorter duration than each video frame period of said predetermined television signal format.

2. An endoscope according to claim 1 wherein said accessory means are a high frequency surgical knife insertable through a channel defined in said insertion member for inserting a medical instrument.

3. An endoscope according to claim 1 wherein said accessory means are DC-DC converter means installed in an operating means of said endoscope.

4. An endoscope according to claim 1 wherein said accessory means; are ultrasonic diagnostic means provided with ultrasonic probes formed of ultrasonic vibrators emitting ultrasonic waves under application of high frequency pulses thereto, and disposed at the tip of said insertion member.

5. An endoscope according to claim 1 wherein said solid state optical image pickup is of a line transferring type and includes means for reducing a signal reading-out period thereof.

6. An endoscope according to claim 1 wherein said solid state optical image pickup is formed of a plurality of photo-electrically converting receiver element means arranged in plural regular horizontal rows for each storing electrical charge signals corresponding to incident illumination received thereon and transmitting said electrical charge signals successively horizontally therealong under application of said clock signals thereto, and a plurality of shift register means each in operable association with said rows of receiver elements and each having an output terminal, for reducing a reading-out period of said charge signals from said pickup by dividing the signal output of said pickup into plural channels each employing one of said plurality of shift registers.

7. An endoscope according to claim 1 wherein said control gate generator means includes means for outputting a low level control gate signal during which said accessory means is switched off and said solid state optical image pickup is read out during this low level signal.

8. An endoscope according to claim 1 including a synchronizing means for causing an operating period of said accessory means to coincide with a storage period of said solid state optical image pickup said storage period being when said solid state optical image pickup is under illumination by said illuminating means.

* * * * *